US00PP09058P

United States Patent [19]

Fruehwirth

[11] Patent Number: Plant 9,058

[45] Date of Patent: Feb. 14, 1995

[54] POINSETTIA PLANT '664'

[75] Inventor: Franz Fruehwirth, Encinitas, Calif.

[73] Assignee: Paul Ecke Ranch, Encinitas, Calif.

[21] Appl. No.: 192,442

[22] Filed: Feb. 7, 1994

[51] Int. Cl.[6] ..... A01H 5/00

[52] U.S. Cl. ..... Plt./86.4

[58] Field of Search ..... Plt. 86.4

*Primary Examiner*—James R. Feyrer

*Attorney, Agent, or Firm*—Arnold, White & Durkee

[57] ABSTRACT

Poinsettia '664' is a new cultivar, distinguished by bright red, erect flower bracts, early flowering and self-branching characteristics. '664' is a naturally occurring sport of the poinsettia '268' (U.S. Plant Pat. No. 7,275) with the same cultural requirements. The new plant produces a very desirable, early flowering, branched pot plant.

1 Drawing Sheet

BACKGROUND OF THE NEW PLANT

This new poinsettia cultivar, '664', originated as a natural early flowering sport of poinsettia '268' (U.S. Plant Pat. No. 7,275) in my greenhouse in Encinitas, Calif. The new plant was grown under the same conditions as other cuttings taken from the parent '268'. It was selected from among several thousand successive tip cuttings taken from the mature parent '268' over a period of several months starting in early March. It was selected because of its early flowering, bright red, erect flower bracts and self branching characteristics; traits which distinguish it from other poinsettia cultivars, and seem to make it a desirable plant for commercial greenhouse production. Under the same cultural and environmental conditions, '664' had less leaves than '268,' perhaps indicating an earlier flower initiation date. Also, '664' was shorter and reached full maturity 10 days earlier than '268'. Otherwise, '664' had the same characteristics and cultural requirements as its parent, '268'. Poinsettia '664' offers certain economic advantages, in that it was in full flower for the early poinsettia market and no chemical growth retardant was needed to control plant height. After selection, '664' was vegetatively reproduced from stem cuttings for test purposes in Encinitas, Calif.

By subjecting clones of this plant to successive generations of vegetative propagation, it was demonstrated that the distinctive characteristics of '664' held true from generation to generation. Clones were taken from tip cuttings of the mature plant and thereafter for at least 3–5 successive generations of the propagated cuttings without any observable changes. From all indications, the plant appeared genetically stable. Additionally, there was no indication of an effect due to chemical treatment or viral infection.

DESCRIPTION OF THE PHOTOGRAPHS

Poinsettia '664' is illustrated in the accompanying color photographs. The upper photo is a side view of 3 single plants per pot in full flower. Evidence of self-branching can be seen in the flowering axillary branches beneath the upper canopy of bracts. The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

The following chart summarizes some of the differences between '268' and '664'.

| Plant | '268' | '664' |
|---|---|---|
| Height | 41 cm | 34 cm |
| No. of Leaves | 20 | 18 |
| Flower response time | 9 weeks | 10 days earlier than '268' |
| Blooming date (Northern hemisphere) | November 20 | November 30 |

Origin: Naturally occurring sport of Poinsettia '268' (U.S. Plant Pat. No. 7,275).

Classification:

*Botanic.*—*Euphorbia pulcherrima* Willd.

*Common name.*—Poinsettia.

*Cultivar name.*—'664'.

Form: Shrub

Height: Short

Growth habit: As a single stemmed plant, upright and vigorous with self-branching side shoots. The plant height of '664' was shorter than '268'. The cultural requirements appear to be the same as for the parent, poinsettia '268'. The application of a chemical growth retardant may not be needed to restrict height for commercial pot plant production. I observed 3 unpinched plants in a pot with an overall height of 34 cm. and an overall width of 48 cm. The bract diameter of individual flowers was 32 cm. By contrast, the overall height of '268' was 41 cm.

Branching: Axillary branches will develop and terminate in a flower without pinching. However, it is usually desirable to pinch '664' before flower induction and remove all terminal dominance. Then, all axillary branches will develop uniformly and at a faster rate.

Growth rate: Rooting of stem cutting occurs in 12–18 days under intermittent mist. The plant will flower in about eight weeks under continuous long night conditions and night temperatures of about 16–18 degrees C. In my greenhouse, poinsettia '664' reached full maturity on November 20. Poinsettia '268' reached full maturity on November 30.

Foliage: The foliage is clean and uniformly green from button to top of the plant. The leaves are of medium size, leaf blades typically being 12–13 cm. long and about 9–10 cm. wide with leaf petioles 5–6 cm. long.

*Leaf shape.*—Typical leaves are generally ovate with acute to obtuse bases and acuminate tips. Leaf margins are entire or lobed with 1 indentation on each side of the leaf blade.

*Color.*—Upper side — Green, near RHS 147A. Under side — Green, near RHS 138A and RHS 147B.

i Retention.—The foliage lasts fairly well even under low light intensities in the consumer's home.

Bracts: Generally there were 20–23 bright red, erect bracts of various sizes subtending the cyathia. The primary bracts are large, have blades typically 14–16 cm. long and 11–12 cm. wide with petioles 3–4 cm. long.

*Shape.*—Bracts are ovate with acute bases and acuminate tips. Primary bracts are lobed with 1 distinctive indentation on either side of the bract.

Secondary bracts are obovate to elliptic and have entire margins.

*Color.*—Upper side — Bright red, between RHS 45A-B. Under side — Red, near RHS 47A and RHS 45C.

Flowers: Generally, 18–21 cyathia (flowers) were present when the plant was in full bloom. Each cyathium is about 8 mm long and 5 mm wide, light green in color, and fringed with red at the distal end. A yellow nectar cup protrudes from the side of each cyathium. The flower pedicel is also light green and about 5–6 mm in length. The stamens protruding from the cyathia are red. The anthers are bifurcate; the pollen is yellow and copious. The stigmas are red and trifurcate. Cyathia retention was about three weeks beyond the time the flower was fully mature.

*Nectar exudate.*—Present, abundant.

*Seed formation.*—Self-incompatible.

*Fertility.*—Not observed.

What is claimed is:

1. A new and distinct Poinsettia cultivar, substantially as herein shown and described, distinguished by its bright red, erect flower bracts, self branching traits and early flowering.

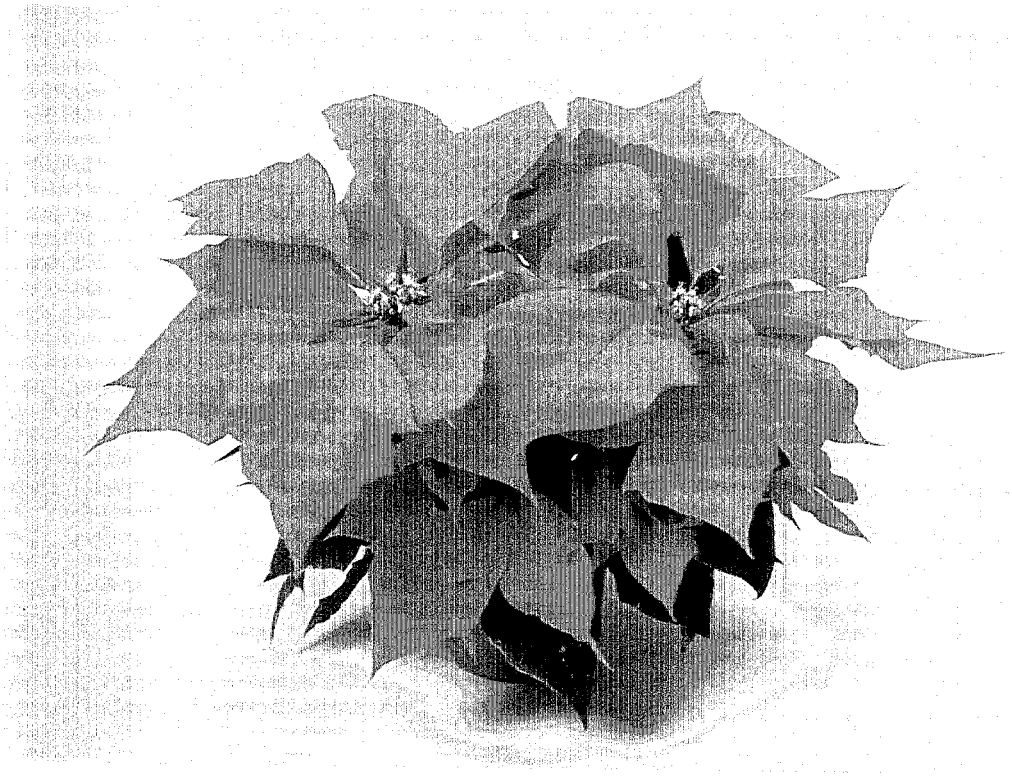
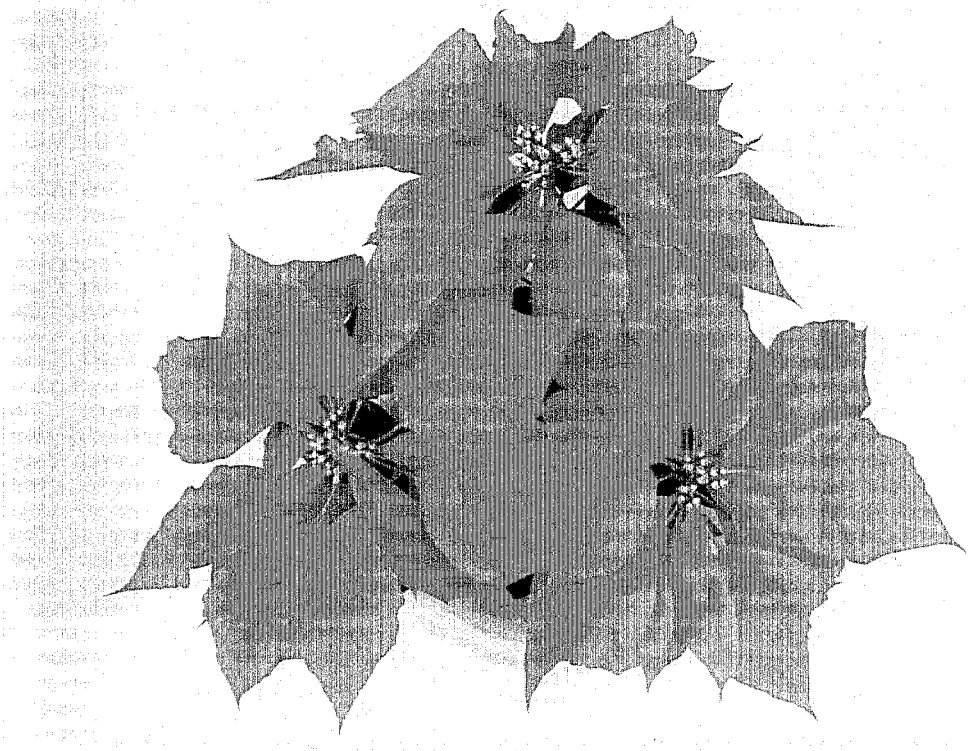

* * * * *